(12) United States Patent
Janovsky et al.

(10) Patent No.: US 8,778,016 B2
(45) Date of Patent: Jul. 15, 2014

(54) METHOD AND APPARATUS FOR REPAIRING OR REPLACING CHORDAE TENDINAE

(75) Inventors: Chris Janovsky, Irvine, CA (US); Christopher Olson, Costa Mesa, CA (US); Hsingching Crystal Hsu, Newport Beach, CA (US); Carl Swindle, Dana Point, CA (US); Erin Glines, Irvine, CA (US); Ian Shakil, Irvine, CA (US); Pooja Sharma, Irvine, CA (US); Stanton Rowe, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1306 days.

(21) Appl. No.: 12/191,408

(22) Filed: Aug. 14, 2008

(65) Prior Publication Data
US 2010/0042147 A1    Feb. 18, 2010

(51) Int. Cl.
*A61F 2/24*    (2006.01)
*A61B 17/04*    (2006.01)
*A61B 17/00*    (2006.01)

(52) U.S. Cl.
CPC ..... *A61B 17/0401* (2013.01); *A61B 2017/0441* (2013.01); *A61B 17/0487* (2013.01); *A61F 2/2457* (2013.01); *A61B 2017/00243* (2013.01); *A61B 2017/0464* (2013.01); *A61B 2017/0417* (2013.01); *A61B 2017/00292* (2013.01); *A61F 2/2463* (2013.01); *A61B 2017/0409* (2013.01); *A61B 2017/00783* (2013.01)
USPC .............................. 623/2.1; 623/2.11; 600/37

(58) Field of Classification Search
USPC ............ 623/2.1–2.19, 2.36, 2.37, 23.72, 904; 606/151, 155, 159, 228; 128/898; 600/37
See application file for complete search history.

(56) References Cited

U.S. PATENT DOCUMENTS

| | | | |
|---|---|---|---|
| 5,522,876 A | 6/1996 | Rusink | |
| 5,662,704 A | 9/1997 | Gross | |
| 6,332,893 B1 | 12/2001 | Mortier et al. | |
| 6,358,277 B1 | 3/2002 | Duran | |
| 6,629,534 B1 | 10/2003 | St. Goar et al. | |
| 6,986,775 B2 | 1/2006 | Morales et al. | |
| 6,997,950 B2 | 2/2006 | Chawla | |
| 7,004,176 B2 | 2/2006 | Lau | |
| 7,083,628 B2 | 8/2006 | Bachman | |
| 7,094,244 B2 | 8/2006 | Schreck | |
| 7,112,207 B2 | 9/2006 | Allen et al. | |
| 7,270,669 B1 | 9/2007 | Sra | |
| 7,381,210 B2 | 6/2008 | Zarbatany et al. | |
| 7,431,692 B2 | 10/2008 | Zollinger et al. | |
| 7,562,660 B2 * | 7/2009 | Saadat | 128/898 |
| 7,632,308 B2 * | 12/2009 | Loulmet | 623/2.1 |
| 7,635,386 B1 * | 12/2009 | Gammie | 623/2.11 |
| 7,871,368 B2 * | 1/2011 | Zollinger et al. | 600/37 |
| 2002/0116027 A1 * | 8/2002 | Egan et al. | 606/228 |
| 2003/0093118 A1 | 5/2003 | Ho et al. | |

(Continued)

*Primary Examiner* — Melanie Tyson
*Assistant Examiner* — Todd J Scherbel
(74) *Attorney, Agent, or Firm* — Klarquist Sparkman, LLP

(57) ABSTRACT

A method and apparatus for performing mitral valve chordal repair on a patient include attaching at least one filament to a mitral valve leaflet and to a papillary muscle. A first end of a filament can be attached to the mitral valve leaflet and the length of the filament can be adjusted by adjusting the tension of the filament in a catheter. The second end of the filament can be attached to an attachment site.

14 Claims, 13 Drawing Sheets

(56) References Cited

U.S. PATENT DOCUMENTS

| | | | |
|---|---|---|---|
| 2003/0105519 A1 | 6/2003 | Fasol et al. | |
| 2004/0106989 A1 | 6/2004 | Wilson et al. | |
| 2007/0100439 A1 | 5/2007 | Cangialosi et al. | |
| 2007/0112422 A1 | 5/2007 | Dehdashtian | |
| 2007/0118151 A1* | 5/2007 | Davidson | 606/144 |
| 2007/0118154 A1* | 5/2007 | Crabtree | 606/151 |
| 2007/0118213 A1* | 5/2007 | Loulmet | 623/2.1 |
| 2007/0213582 A1* | 9/2007 | Zollinger et al. | 600/37 |
| 2008/0195126 A1* | 8/2008 | Solem | 606/155 |
| 2008/0228272 A1* | 9/2008 | Moaddeb et al. | 623/13.13 |
| 2009/0043153 A1* | 2/2009 | Zollinger et al. | 600/37 |
| 2009/0088837 A1* | 4/2009 | Gillinov et al. | 623/2.1 |
| 2009/0270980 A1 | 10/2009 | Schroeder et al. | |
| 2010/0023118 A1* | 1/2010 | Medlock et al. | 623/2.11 |
| 2010/0204716 A1* | 8/2010 | Stewart et al. | 606/142 |
| 2011/0011917 A1* | 1/2011 | Loulmet | 227/181.1 |

\* cited by examiner

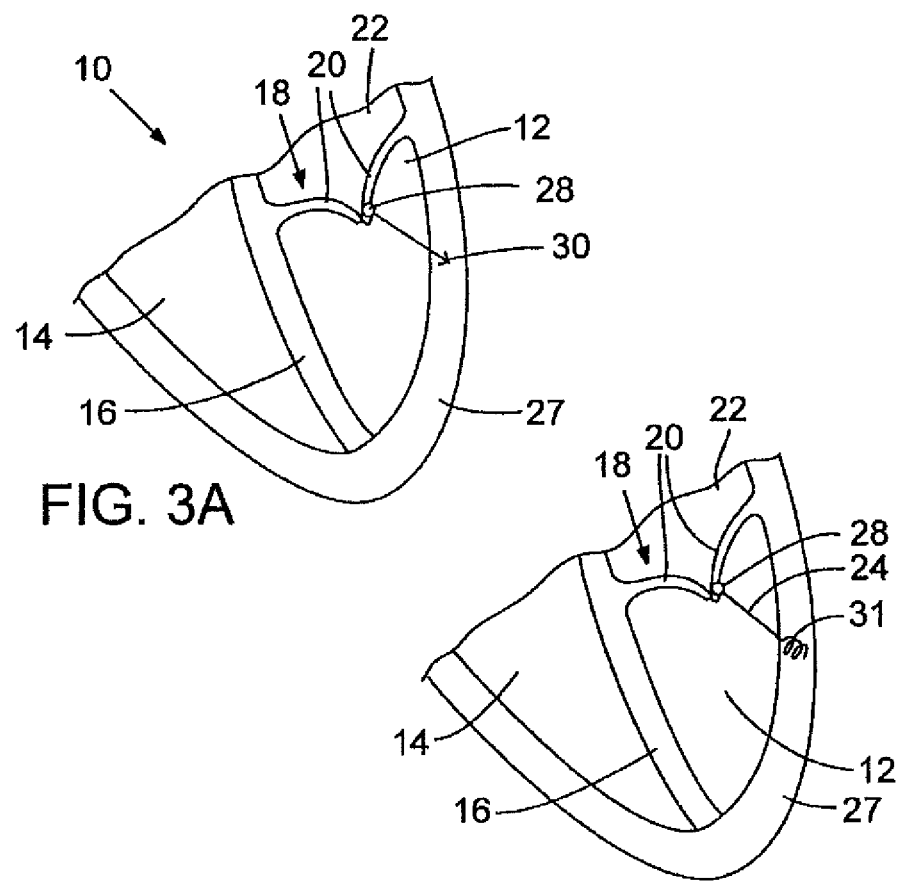
FIG. 3A
FIG. 3B
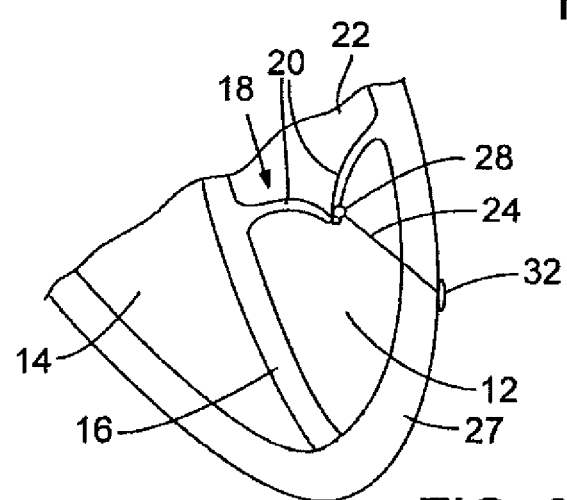
FIG. 3C

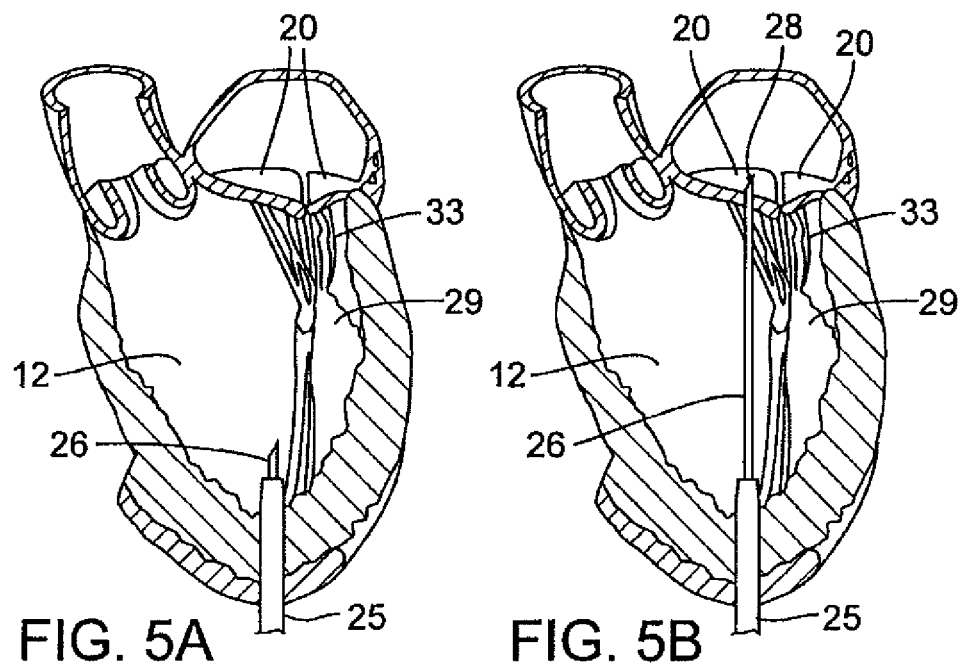

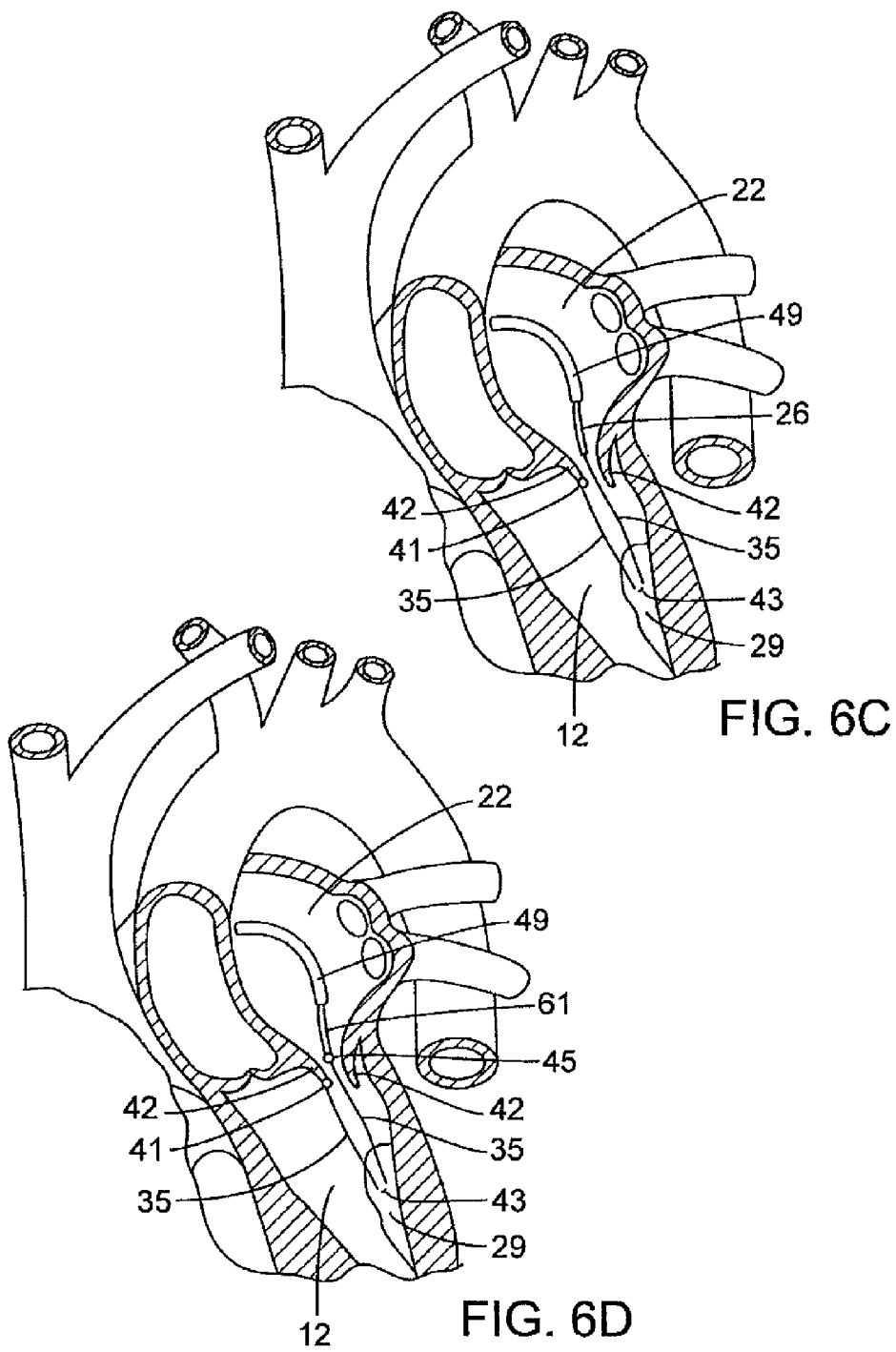

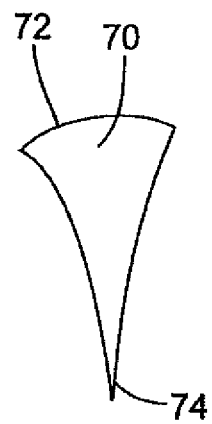
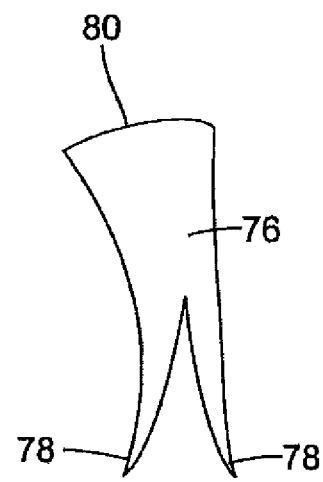
FIG. 7    FIG. 8
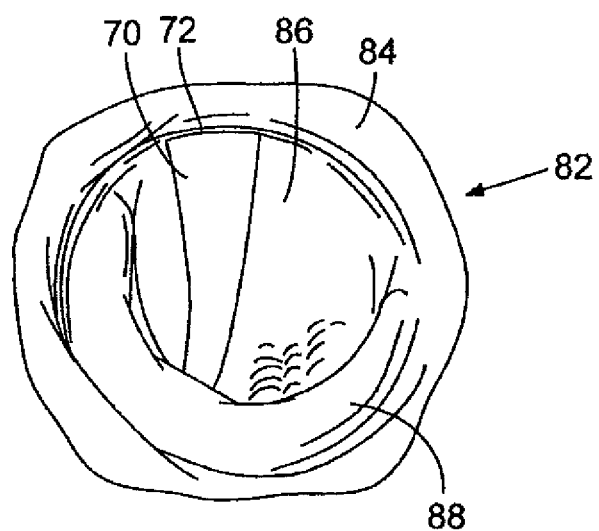
FIG. 9

METHOD AND APPARATUS FOR REPAIRING OR REPLACING CHORDAE TENDINAE

BACKGROUND

The present disclosure concerns methods and apparatuses for replacing, repairing, or supplementing chordae tendinae to improve or restore the connection of the mitral leaflets to the heart wall.

DESCRIPTION OF THE RELATED ART

Mitral regurgitation is a valvular heart disease that results in the abnormal leaking of blood through the mitral valve, from the left ventricle into the left atrium of the heart. The mitral valve includes valve leaflets and a mitral valve annulus that forms a ring around the valve leaflets. Chordae tendineae connect the valve leaflets to the papillary muscles, which tether the valve leaflets to the left ventricle and prevent them from prolapsing into the left atrium. Mitral regurgitation can result from the dysfunction of any of these portions of the mitral valve.

In some patients with mitral regurgitation, the abnormal leakage of blood is caused, at least in part, from damaged chordae. The chordae can be, for example, elongated or torn, which can cause the mitral valve to function improperly. Artificial chordae can be used to supplement or replace damaged chords to attempt to improve mitral valve functioning. It is important that the artificial chordae be selected to be a proper length so that they serve the desired purpose and, at the same time, do not cause additional stresses to the heart itself. Known methods of implementing artificial chordae, however, fail to provide precise mechanisms for adjusting the length of the artificial chords while maintaining the anatomy of both the valve and the papillary muscle.

Moreover, traditional methods of chordae replacement often require patients to undergo open heart surgery with a bypass machine. In addition to being highly invasive and causing significant stress and trauma to the patient, these methods require surgeons to estimate proper chordae length in an environment that does not properly reflect the normal beating heart.

SUMMARY

Preferred embodiments of the present disclosure are directed toward new and non-obvious methods and apparatuses for performing mitral valve chordal repair on a patient while the patient's heart is beating.

In one embodiment, a method is disclosed that includes making an incision in a ventricular wall of a patient at or near a papillary muscle, inserting a catheter through the incision into a left ventricle of the patient, and attaching a first end of a filament to a mitral valve leaflet. The catheter can be at least partially withdrawn from the left ventricle and a distal end of the catheter can be navigated to a position at or near the incision. The position can be at or near an attachment site where a second end of the filament is to be attached to the papillary muscle or ventricular wall. The length of the filament can be adjusted by adjusting the tension of the filament in the catheter while substantially holding the catheter at the position, and the second end of the filament can be attached to the attachment site.

In another embodiment, a method is disclosed that includes making an incision in a ventricular wall of a patient, inserting a catheter through the incision into a left ventricle of the patient, and attaching a first end of a filament to a mitral valve leaflet. A distal end of the catheter can be navigated to a position at or near a papillary muscle, which is at or near an attachment site where a second end of the filament is to be attached to the papillary muscle. The catheter can be held at the position, the length of the filament can be adjusted by adjusting the tension of the filament in the catheter, and the second end of the filament can be attached to the attachment site. The catheter can optionally be held at the position by a suction device or a clamping device.

In another embodiment, a method is disclosed that includes navigating a catheter percutaneously via a patient's vasculature into a left atrium of the patient and navigating the catheter through the left atrium and into a left ventricle of the patient. A first end of a filament can be attached to a mitral valve leaflet. A distal end of the catheter can be navigated to a position at or near a papillary muscle, which is at or near an attachment site where a second end of the filament is to be attached to the papillary muscle. The second end of the filament can be temporarily attached to the attachment site and the catheter can be retracted from the left ventricle into the left atrium. The effect of the filament on the beating heart can be observed and the length of the filament can be adjusted. The second end of the filament can be permanently attached to the attachment site. Optionally, the filament can be temporarily attached to the attachment site by using a clip or a temporary suturing technique. In addition, the length of the filament can optionally be adjusted by adjusting the tension of the filament in the catheter.

In another embodiment, a method is disclosed that includes navigating a catheter percutaneously via a patient's vasculature into the left atrium of the patient, inserting the catheter into the left ventricle of the patient through the mitral valve, and attaching a first end of a filament to a first mitral valve leaflet. A second end of the filament can be passed through a first papillary muscle of the patient at an attachment site. The catheter and the second end of the filament can be withdrawn from the left ventricle into the left atrium. The length of the filament can be adjusted by adjusting the tension of the filament in the catheter, and the filament can be attached to the attachment site.

Optionally, the filament can be attached to the attachment site by advancing a clip along the filament to the attachment site and securing the clip to the filament at the attachment site. The second end of the filament can optionally be passed through a second papillary muscle at a second attachment site prior to withdrawing the catheter and the second end of the filament from the left ventricle. In addition, the second end of the filament can optionally be attached to a second mitral valve leaflet.

In another embodiment, a method of improving the functioning of native mitral valve leaflets is disclosed. A catheter contains at least one triangular shaped member. The triangular shaped member has a short side and at least one point opposite the short side. The method comprises inserting the catheter into the left ventricle of the patient; attaching the short side of the triangular shaped member to the valve annulus of the mitral valve; and attaching the at least one point opposite the short side of the triangular shaped member to a papillary muscle of the patient.

Optionally, the method can further comprise shortening the effective length of the triangular shaped member by applying tension to a length adjustment member that extends along at least a portion of the triangular shaped member.

Optionally, the method can further comprise shortening the effective length of the triangular shaped member by sewing up slack in the triangular shaped member at the ring annulus.

Optionally, the triangular shaped member can comprise two points opposite the short side, with each of the two points being attached to the papillary muscle of the patient.

Optionally, the triangular shaped member can further comprise at least a portion of a ring attached to the short side of the triangular shaped member, and the method can further comprise attaching the at least a portion of the ring to the valve annulus.

In another embodiment, a triangular shaped member for attachment to a valve annulus of a mitral valve and a papillary muscle of a patient is disclosed. The triangular shaped member comprises a short side and at least one point opposite the short side, and a length adjustment member extending along at least a portion of the triangular shaped member. The short side of the triangular shaped member is configured for attachment to the valve annulus and the at least one point opposite the short side of the triangular shaped member is configured for attachment to the papillary muscle of the patient. The length adjustment member is configured to adjust the effective length of the triangular shaped member when tension is applied to the length adjustment member.

Optionally, the triangular shaped member can further comprise at least a portion of a ring attached to the short side of the triangular shaped member.

In another embodiment, a method of performing mitral valve chordal repair on a patient while the patient's heart is beating is disclosed. The method comprises: navigating a distal end of a catheter to a mitral valve leaflet of the patient. The catheter contains at least one filament, with the filament having a first end and a second end. The method further comprises passing the first end of the filament through a first attachment point at the mitral valve leaflet; navigating the distal end of the catheter to a position at or near a papillary muscle, the position being at or near a second attachment point on the papillary muscle; passing the first end of the filament through the second attachment point; adjusting the length of the filament by adjusting tension of the filament in the catheter; passing the first end of the filament through a securing device; and securing the first end of the filament to another portion of the filament using the securing device.

Optionally, the step of adjusting the length of the filament can further comprise passing the first end of the filament into the catheter to facilitate manual adjustment of tension of the filament in the catheter.

Optionally, the first attachment point comprises an anchor with an eyelet. Optionally, the second attachment point comprises a moveable stitch. Optionally, the securing device comprises a zip-tie device.

In another embodiment, a method of performing mitral valve chordal repair on a patient while the patient's heart is beating is disclosed. The method comprises attaching a first anchor device to a papillary muscle of the patient, the first anchor device comprising an eyelet for receiving a filament; attaching a second anchor device to a mitral valve leaflet of the patient, the second anchor device comprising an eyelet for receiving a filament; forming a filament loop by passing a first end of the filament through the eyelet of the first anchor device and the eyelet of the second anchor device; and fixing the length of the filament between the first and second anchor devices using a securing device.

Alternatively, the method further comprises passing the first end of the filament back into the catheter after forming the filament loop, and adjusting the length of the filament between the first and second anchor devices by adjusting the tension of the filament in the catheter.

Optionally, the securing device comprises a clip secured to the filament at the first anchor device. Alternatively, the securing device comprises a weld securing the filament to itself at a point along the filament loop.

BRIEF DESCRIPTION OF THE DRAWINGS

FIG. 3A is a view of an embodiment of a method and apparatus for attaching artificial chordae to a valve leaflet.

FIG. 3B is a view of an embodiment of a method and apparatus for attaching artificial chordae to a valve leaflet.

FIG. 3C is a view of an embodiment of a method and apparatus for attaching artificial chordae to a valve leaflet.

FIG. 5A is a sectional view of another embodiment of a method and apparatus for attaching artificial chordae to a valve leaflet.

FIG. 5B is a sectional view of another embodiment of a method and apparatus for attaching artificial chordae to a valve leaflet.

FIG. 6C is a sectional view of another embodiment of a method and apparatus for attaching artificial chordae to valve leaflets using a percutaneous method.

FIG. 6D is a sectional view of another embodiment of a method and apparatus for attaching artificial chordae to valve leaflets using a percutaneous method.

FIG. 7 is a side view of a triangular shaped member for attachment to a valve annulus and a papillary muscle.

FIG. 8 is side view of another triangular shaped member for attachment to a valve annulus and a papillary muscle.

FIG. 9 is a top view of a triangular shaped member attached to a valve annulus.

DETAILED DESCRIPTION

The present disclosure relates to methods and apparatuses for providing mitral valve chordal repair that permits the mitral valve leaflets to be attached to the papillary muscles or ventricular wall in a manner that is both minimally invasive and/or that permits chordal length adjustments.

Figure 1:
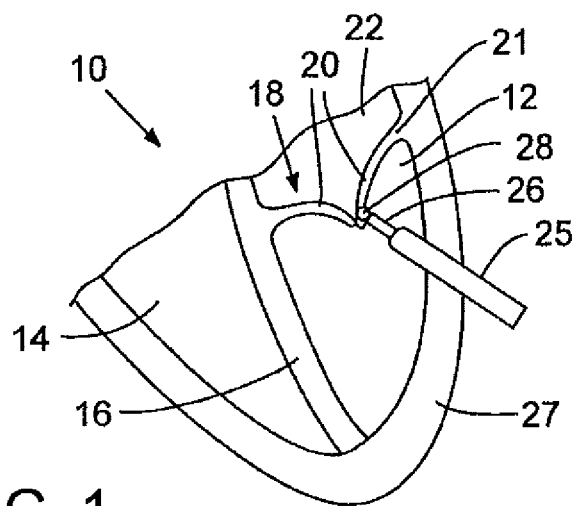
FIG. 1 is a view of an embodiment of a method and apparatus for attaching artificial chordae to a valve leaflet.

FIGS. 1-4 illustrate one embodiment of a method for mitral valve chordal repair that is minimally invasive and permits adjustment of the length of the artificial chordae. FIG. 1 depicts a schematic portion of a human heart 10. Heart 10 includes left ventricle 12, right ventricle 14, and septum 16. The mitral valve 18 includes valve leaflets 20, the mitral valve annulus 21, the papillary muscles (not shown), and the chordae tendineae (not shown). The chordae connect the valve leaflets to the papillary muscle in the left ventricle to prevent them from prolapsing into the left atrium 22. One or more filaments 24 can be attached to valve leaflets 20 in the event that the natural chordae have failed or are otherwise not properly acting to prevent prolapse of the valve leaflets into the left atrium.

As shown in FIG. 1, a delivery system comprises a deployment catheter 26 that contains two fastening mechanisms connected by a filament 24 (artificial chordae) and an introducer sheath system 25 to access the mitral valve leaflets. The introducer sheath enters the left ventricle through an incision in the chest wall and ventricular wall 27. The incision is desirably made near or at the location of the papillary muscles. Two concentric rings of purse-string sutures can be used around the incision in the left ventricular wall to maintain a good seal around the introducer sheath. For convenience and to show the catheter systems disclosed herein more clearly, the introducer sheath is omitted from the majority of the figures. However, it should be noted that an introducer sheath can be used in each embodiment disclosed herein.

The deployment catheter 26 passes through the sheath and a distal end of the catheter advances to mitral valve leaflet 20. The valve leaflet can be captured on the distal end of the catheter by a vacuum system or some other capturing mechanism via the catheter. The catheter may have a steering mechanism that is operable to selectively bend or adjust the curvature of the catheter. Such a steering mechanism can assist in accessing the valve leaflets, as well as to help maneuver the catheter to the other areas of the heart or body discussed herein. Once the valve leaflet is captured, catheter 26 deploys a fastening mechanism 28 to be fastened to valve leaflet 20.

First fastening mechanism 28 can be any fastener that is traditionally used to secure elements within the heart. For example, first fastening mechanism 28 could be a clip, staple, tying, or suture type fastener. The first fastening mechanism is desirably made of a material that is visible on fluoroscopy or other imaging technology to aid in placement of the fastener during the procedure.

First fastening mechanism 28 is attached to the filament 24. Filament 24 can be pre-attached to the first fastening mechanism. That is, filament 24 can have first fastening mechanism 28 attached to it outside the body prior to entering the left ventricle. Alternatively, the filament can be attached to the first fastening mechanism within the left ventricle after the fastening mechanism is attached to the valve leaflet.

Figure 2:
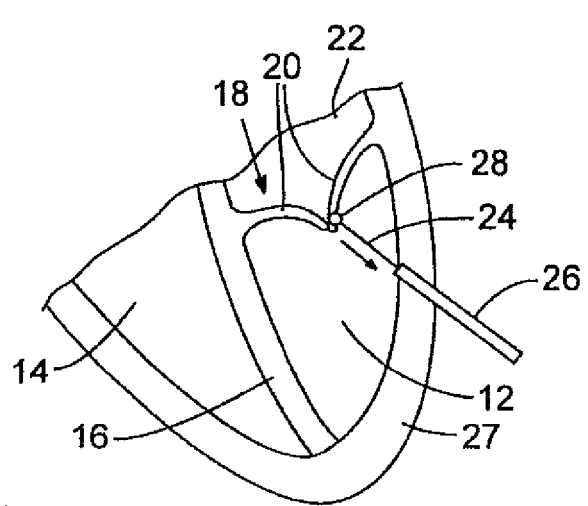
FIG. 2 is another view of the embodiment shown in FIG. 1.

As shown in FIG. 2, after first fastening mechanism 28 and filament 24 are coupled to valve leaflet 20, the catheter 26 can be at least partly withdrawn from the left ventricle in the general direction of the arrow shown in FIG. 2. Catheter 26 is desirably withdrawn to the vicinity of where the filament will be attached to the papillary muscle or ventricular wall and the length of the filament is changed by adjusting the tension of the filament through the catheter. Desirably, a physician can observe the beating heart of the patient via imaging technology and make appropriate filament length adjustments based on those observations.

Once the filament is adjusted to the desired length, the filament can be secured to a second fastening mechanism, which is deployed to anchor the filament to an area of the ventricular wall near the point of the incision. The second fastening mechanism can be secured to the papillary muscle, to the ventricular wall, or to the outside of the ventricular wall. The second fastening mechanism is desirably made of a material that is visible on fluoroscopy to aid in its placement during the procedure.

As shown in FIG. 3A, the second fastening mechanism can be implanted in the ventricular wall itself. FIG. 3A depicts an anchor 30 securing the filament to the ventricular wall. Anchor 30 may be a multi-barbed anchor. Alternatively, the second fastening member can be any other type of traditional securing device, such as the screw mechanism 31 depicted in FIG. 3B.

If desired, the second fastening mechanism can instead be attached outside the ventricular wall as shown in FIG. 3C. FIG. 3C depicts a disk 32 that anchors the filament to the heart at a location outside of the heart. The disk can be a self-expanding disk that expands once it is deployed from the delivery catheter.

By accessing the left ventricle through an incision at or near the papillary muscles as discussed above, the desired length of the filament can accurately determined and the filament easily adjusted to that desired length. The location of the incision permits the distal end of the catheter to be withdrawn to the approximate point of attachment at the papillary muscle site. Once the catheter is withdrawn to the location of the papillary muscles, the length of the filament can be accurately adjusted by adjusting the tension of the filament through the catheter.

Figure 4A:
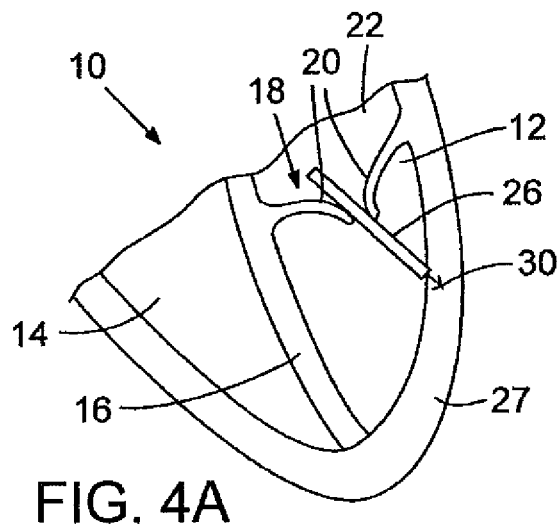
FIG. 4A is a view of an embodiment of a method and apparatus for attaching artificial chordae to a valve leaflet.
Figure 4B:
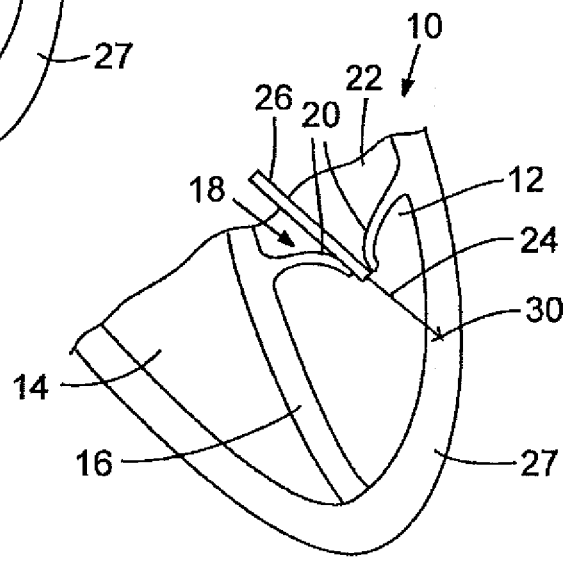
FIG. 4B is a view of an embodiment of a method and apparatus for attaching artificial chordae to a valve leaflet.
Figure 4C:
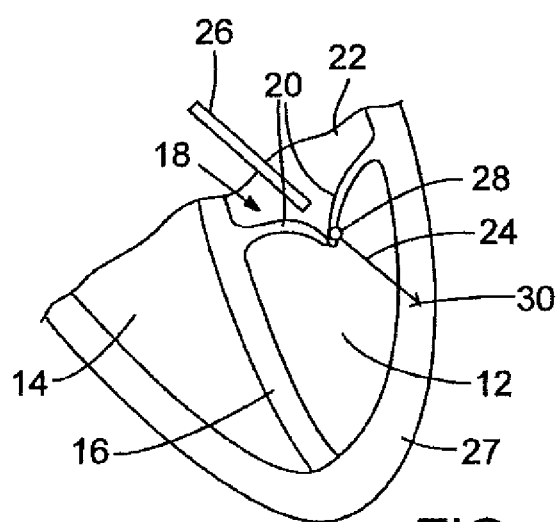
FIG. 4C is a view of an embodiment of a method and apparatus for attaching artificial chordae to a valve leaflet.

FIGS. 1-3 depict an embodiment where the left ventricle is accessed through incisions in the chest and ventricular wall. Alternatively, the left ventricle can be accessed percutaneously. If it was desired to perform the above method percutaneously, the mitral valve can be accessed, for example, through a transfemoral procedure. FIGS. 4A-4C illustrate an embodiment of this method where entry into the left ventricle by a device comprising a deployment catheter is made through the left atrium. Procedures for gaining percutaneous access to the left atrium are known. For example, U.S. Patent Publication No. 2004/0181238, which is incorporated herein by reference, provides additional details for accessing the mitral valve via the femoral or jugular veins.

FIG. 4A depicts a catheter 26 passing through the mitral valve 18 and into the left ventricle 12. Catheter 26 is maneuvered to a location at or near the papillary muscles and a filament 24 is attached to the papillary muscles via anchor 30. Anchor 30 may be a multi-barbed anchor. Alternatively, the filament can be secured to the papillary muscle using any other type of traditional securing device, such as, for example, the screw mechanism 31 depicted in FIG. 3B.

After one end of the filament is secured to the papillary muscles, catheter 26 is withdrawn from the left ventricle to a location at or near valve leaflets 20, as shown in FIG. 4B. Catheter 26 is desirably maneuvered to the approximate location on a valve leaflet where the other end of the filament is to be attached. By maneuvering to this location, the physician can adjust the tension of the filament in the catheter to alter the length of the filament, desirably while observing the beating heart of the patient using imaging technology.

Once the appropriate adjustments of the filament length are made, the filament is attached to the valve leaflet using fastening mechanism 28. As discussed above, fastening mechanism 28 can be any fastener that is traditionally used to secure elements within the heart. For example, first fastening mechanism 28 could be a clip, staple, tying, or suture type fastener. The fastening mechanism is desirably made of a material that is visible on fluoroscopy or other imaging technology to aid in placement of the fastener during the procedure.

After securing the filament end to the valve leaflets, loose ends of the filament can be cut and removed. This procedure can be repeated as necessary, depending on the number of artificial chordae to be placed within the patient.

Figure 5C:
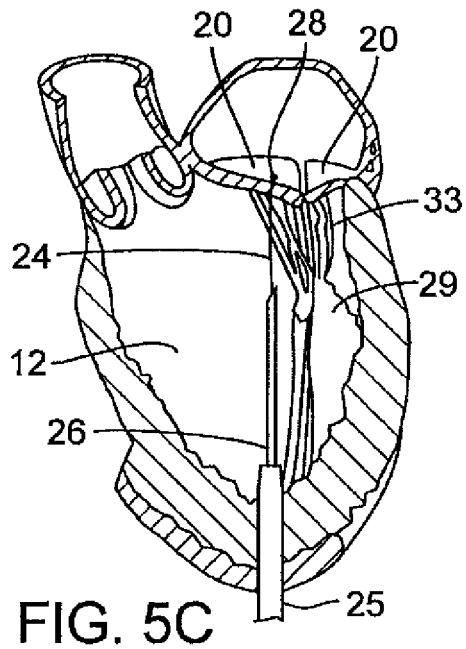
FIG. 5C is a sectional view of another embodiment of a method and apparatus for attaching artificial chordae to a valve leaflet.

FIGS. 5A-5E depicts an embodiment for performing minimally invasive mitral valve repair using a transapical procedure. FIG. 5A schematically illustrates an internal structure of a heart, including the left ventricle 12, mitral valve leaflets 20, papillary muscles 29, and chordae tendinae 33. An incision is made in the chest of a patient and in the ventricle wall of the heart. Introducer sheath system 25 accesses the left ventricle 12 through the incisions, which is desirably made at or near the apex of the heart. Catheter 26 is deployed via the introducer sheath 25 into the left ventricle 12.

Figure 5D:
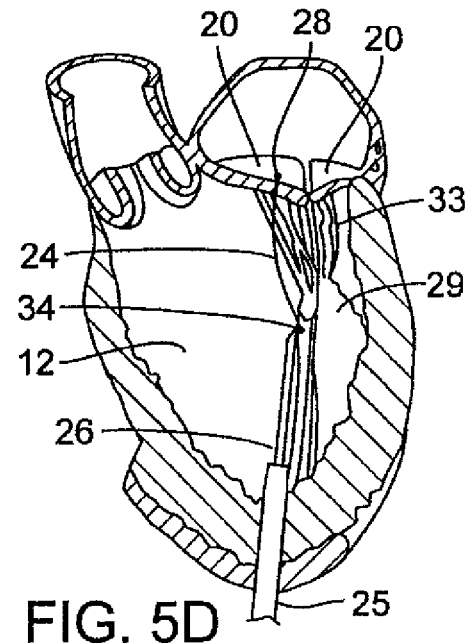
FIG. 5D is a sectional view of another embodiment of a method and apparatus for attaching artificial chordae to a valve leaflet.

As shown in FIG. 5B, catheter 26 can be maneuvered to the area of a valve leaflet 20. Valve leaflet 20 can be captured and a filament can be attached to valve leaflet 20 using fastening mechanism 28 in the manner shown in FIG. 1 and discussed in detail above. Rather than retracting catheter 26 out of the left ventricle towards the point of entry into the left ventricle (as illustrated in FIG. 2), however, the catheter tip is navigated to the area of the papillary muscle 29 as shown in FIG. 5D. The guiding of the catheter, filament, or fastening devices can optionally be assisted by using fluoroscopy or other imaging technology.

One end of filament 24 is now secured to valve leaflet 20 and another end is positioned proximate the papillary muscle with the filament permitted to flow or spool freely from the catheter at that point. Rather than permanently attach the free flowing end of the filament to an anchor point at this time, the catheter can be temporarily held in position by holding mechanism 34. Holding mechanism 34 temporarily secures the catheter to an area at or near the papillary muscle so that the length of the filament can be more accurately adjusted.

Catheter 26 (but not the filament) can be held in place against the papillary muscle, without any permanent anchoring, so that the length of the filament can be adjusted with the heart operating in its normal anatomical condition. Catheter 26 can include a tension adjustment mechanism located outside the body that is operable to increase or decrease the slack in the filament so as to adjust the length of filament inside the heart.

Holding mechanism 34 can be a suction mechanism at the catheter tip to hold the catheter in place. Holding mechanism 34 can alternatively be a pinching, clamping, or hooking mechanism at the tip of the catheter that causes minimal damage to surrounding tissue and chordae. Alternatively, the catheter can be held in place by a temporary suturing technique that does "not fully tie the not." While the catheter is held in place against or adjacent the papillary muscle by holding mechanism 34, the length of the filament can be adjusted to the desired length.

In order to achieve conditions that are sufficiently representative of the beating heart's natural dynamic anatomy, the holding mechanisms discussed herein desirably hold the catheter in place against (or adjacent to) the papillary muscle without imparting significant forces to the papillary muscle anchoring site. By holding the catheter at the papillary muscle anchoring site in the manner described herein, the catheter can gently move with the heart while it rotates and beats. Accordingly, the catheter can be held in a position convenient to make adjustments to the tension or length of the filament, while not significantly altering or affecting the vector forces between the papillary muscle and the leaflet in the heart's natural condition.

Figure 5E:
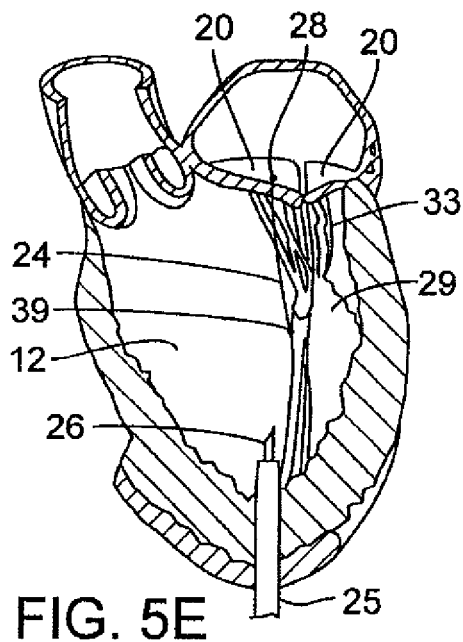
FIG. 5E is a sectional view of another embodiment of a method and apparatus for attaching artificial chordae to a valve leaflet.

As shown in FIG. 5E, once the desired length of the filament 24 has been achieved, the physician can permanently anchor the filament 24 at or near the papillary muscle 29 using anchoring mechanism 39. The permanent anchoring can be achieved by using a permanent suturing or clamping technique. Alternatively, it can entail deploying a different anchoring mechanism, such as a multi-barbed anchor or screw mechanism as discussed above. It should be noted that the use of the term "permanent" or "permanently" herein, in connection with an anchoring or securing mechanism (or the like), does not require or suggest that the anchoring or securing mechanism is incapable of being removed or otherwise releasing its hold on the natural or artificial object to which it is connected.

After securing the filament in a more permanent manner, loose suture remains can be cut and removed, for example, by a tool introduced through introducer sheath 25. Such a tool could be located on either the catheter described above or a different catheter. The foregoing procedures can be repeated as needed to implant additional filaments, and the physician can observe the beating heart and the effects of the filaments on the mitral valve to determine if the procedure was acceptable. Once the physician is satisfied with the results, catheter 26 and introducer sheath 25 can be withdrawn from the heart and the incision closed.

By the above method, a physician can implant adjustable chordae into a patient in a minimally invasive manner, and without having to resort to open heart surgery. The physician can also easily adjust the length of the filament before deploying a more permanent fastening mechanism. The delivery system also allows physicians to change the length of an artificial chordae during a beating heart procedure, which permits the physician to more accurately judge the proper length of the artificial chordae and better restore mitral valve function.

In addition, because the point of attachment is at a location other than the apex entry point, several problems can be eliminated or reduced. First, using the apex as an anchor point can complicate future transapical surgeries. Accordingly, the selection of an anchor point at a papillary muscle site and not at the apex eliminates that problem. Second, the attachment of artificial chordae at the apex of the heart can exert an undesirable upward force on the heart. This upward force can negatively affect the existing chordae and result in unwanted changes to the structure of the heart. With the accurate adjustment method described above and the use of an anchor point at the papillary muscles, rather than at the point of entry, the stresses and strains on the heart caused by the introduction of artificial chordac can be reduced.

The method discussed above and illustrated in FIGS. 5A-5E contemplates accessing the heart transapically by making an incision in the chest and ventricular wall. The transapical approach gives the physician the ability to enter the heart without having to navigate through the arterial or venous systems. The catheter also therefore requires minimal steering or positioning to secure the fastening devices or mechanisms to the mitral valve leaflets and the ventricular wall.

Although the method discussed above is performed using a transapical procedure, it can also be accomplished percutaneously. If it was desired to perform the above method percutaneously, the mitral valve can be accessed, for example, through a transfemoral procedure. Except for the point of entry into the heart and the obvious variations that would be required in view of the difference in entry points, the same steps as discussed above can be followed.

Figure 6A:
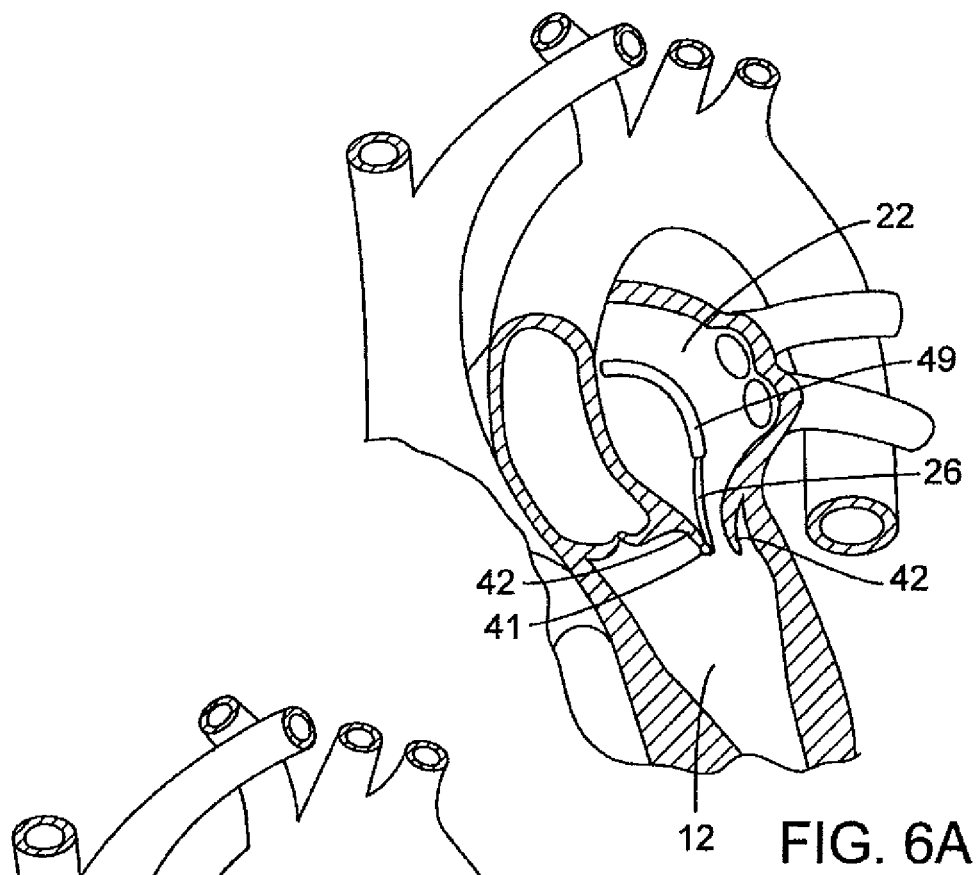
FIG. 6A is a sectional view of another embodiment of a method and apparatus for attaching artificial chordae to valve leaflets using a percutaneous method.

A method of attaching the artificial chordae using a percutaneous transfemoral procedure is illustrated in FIG. 6A. In particular, the transfemoral application involves at least the following steps that differ from the transapical application. Instead of entering into the heart through the chest wall and through the ventricular wall, a small incision can be made to access the femoral vein. An introducer sheath (not shown in FIG. 6A) can be inserted into a femoral vein, and a guide catheter 49 can be navigated through the inferior vena cava, to the right atrium, through the septum, into the left atrium 22. A therapy catheter 26 can then be passed through the guide catheter 49 into the left atrium 22. Catheter 26 can then be navigated through the mitral valve into the left ventricle 12. Alternatively, catheter 26 can be introduced into the right atrium via the right jugular vein. Again, U.S. Patent Publication No. 2004/0181238 (incorporated by reference herein) provides additional details for accessing the mitral valve via the femoral or jugular veins.

Figure 6B:
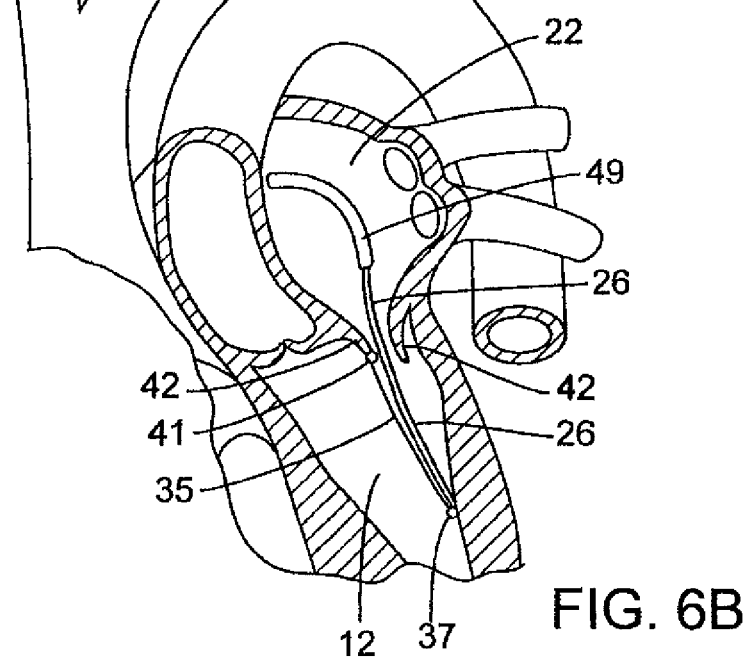
FIG. 6B is another sectional view of the embodiment shown in FIG. 6A.

The basic steps described above can be performed to secure the first fastening mechanism to the valve leaflets and to secure the second fastening mechanism to the papillary muscles and/or ventricular wall. As shown in FIG. 6A, catheter 26 can be used to attach the first fastening mechanism 41 to valve leaflet 42. Filament 35 can be attached to first fastening mechanism 41 (or alternatively, filament 35 can be pre-attached to first fastening mechanism 41, as discussed above). Catheter 26 can then be positioned at or near a papillary muscle as shown in FIG. 6B and the length of filament 35 can be adjusted by adjusting the tension of the filament in the catheter.

Because, in the transfemoral procedure, catheter 26 passes through the mitral valve itself, it may be difficult for a physician to accurately observe the mitral valve in its natural state using the holding mechanism as described above with respect to the transapical approach. Thus, it may be desirable to use a temporary attachment means for temporarily holding the filament at the papillary muscles while catheter 26 is withdrawn from the left ventricle. In order to be able to further observe the effect of the filament on the mitral valve and to determine if the length of the filament has been properly determined, a temporary clip 37 can be placed to hold the filament in place while the catheter 26 is withdrawn from the left ventricle.

Alternatively, filament 35 can be held in place by a temporary suturing technique that can be relatively easily undone if additional adjustments to the length of the filament 35 are required.

Catheter 26 can then be at retracted from the left ventricle 12 so that the valve can be observed under natural conditions. The catheter can be retracted back into the left atrium 22, or, if desired, it can be retracted entirely out of the heart. By using a temporary clip or suture method, the length of the filament can be adjusted, observed, and adjusted again, if necessary. For example, if the physician was not satisfied with the length of the filament after attaching it to the valve leaflet and temporarily attaching it at or near a papillary muscle, the physician can redeploy the catheter into the left ventricle and adjust the length (or tension) of the filament. The adjustment can be made by removing or loosening the temporary clip (or other temporary tying mechanism), thereby permitting the physician to freely adjust the length of the filament. After such an adjustment is made, the physician can reattach the temporary clip (or other temporary holding mechanism). This procedure can be repeated as many times as needed or desired.

Once the desired length is achieved, the filament can be permanently anchored or secured to the papillary muscles, and loose ends of the filament can be cut and removed in the manner discussed above with respect to the transapical approach shown in FIGS. 5A-5E.

Figure 6E:
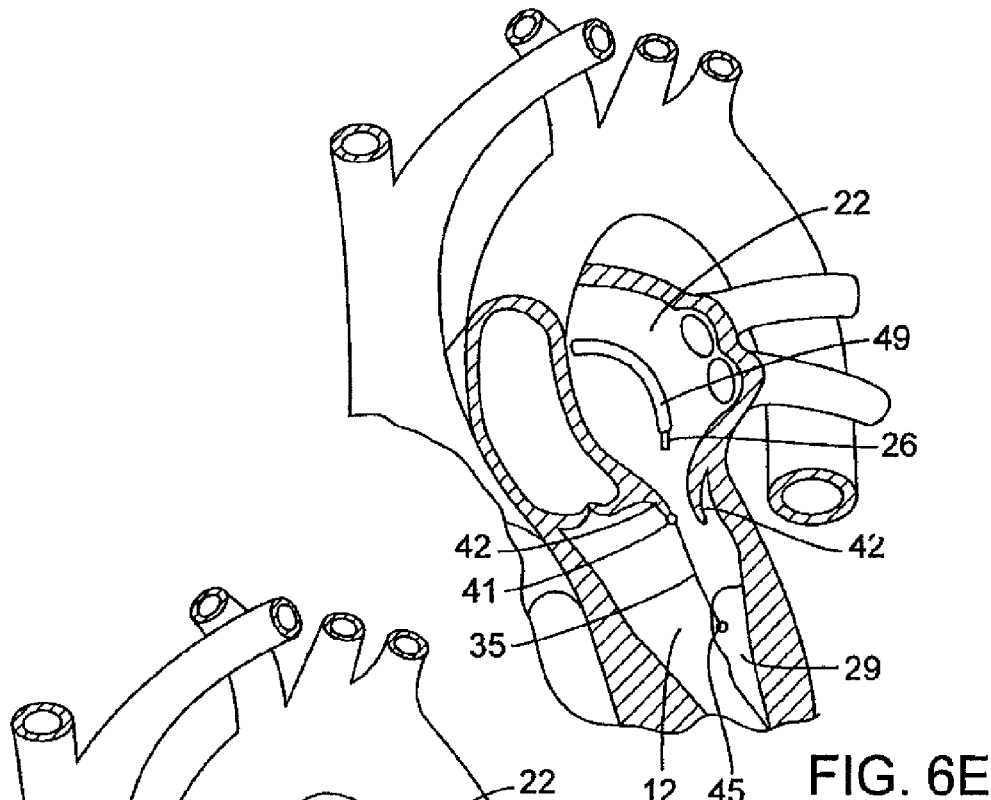
FIG. 6E is a sectional view of another embodiment of a method and apparatus for attaching artificial chordae to valve leaflets using a percutaneous method.

FIGS. 6C, 6D, and 6E depict another method wherein the length of the filament can be adjusted in a percutaneous procedure (for example, transfemoral procedure). Catheter 26 can be used to attach one end of a filament 35 to a valve leaflet 42 using first fastening mechanism 41 in the manner described above and shown in FIG. 6A. Catheter 26 can then be maneuvered to an area near the papillary muscles 29 and filament 35 can be passed through a portion of the papillary muscles at a pass-through area 43. For convenience, a portion of the papillary muscles 29 are schematically represented in FIGS. 6C, 6D, and 6E. Catheter 26 can then be withdrawn back into the left atrium, as shown in FIG. 6C. Because the filament will slide through the pass-through area of the papillary muscles, the length of filament 35 between fastening mechanism 41 and pass-through area 43 can be adjusted by pulling on the filament (i.e., adjusting the tension) using catheter 26. Because the physician can adjust the length of the filament in this manner while observing the heart in its natural state, the physician can accurately determine and select the appropriate length of the filament.

Once the desired length is achieved, a tool 61 can be advanced down the filament from guide catheter 49, and a securing mechanism 45 can be deployed to secure the filament to the papillary muscles. U.S. Patent Publication No. 2004/0181238 (already incorporated by reference above) provides additional details for deploying tools via guide catheters. As shown in FIG. 6E, the securing mechanism 45 holds the filament securely at the papillary muscle 29, desirably at the location of the pass-through area, so that the length of the filament is substantially fixed. The securing mechanism can be any appropriate fastening, anchoring, or securing mechanisms, such as those disclosed herein. For example, the securing mechanism could be a clip holding the filament to the papillary muscle. After the securing mechanism is in place, the loose end of the filament 35 can be cut off and removed from the heart.

Figure 6F:
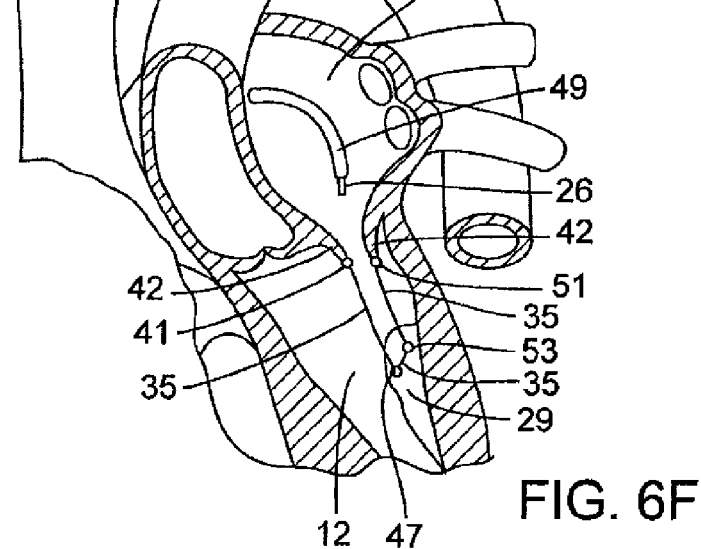
FIG. 6F is a sectional view of another embodiment of a method and apparatus for attaching artificial chordae to valve leaflets using a percutaneous method.

FIG. 6F depicts another embodiment where a single filament is attached to at least two valve leaflets and the papillary muscles 29. In this embodiment, filament 35 is attached to a first valve leaflet 42 via first fastening mechanism 41 in the manner discussed above. Then filament 35 passes through a first papillary pass-through area 47 and a second papillary pass-through area 53. For convenience, first and second papillary pass-through areas are shown schematically as circles in FIG. 6F. However, it is understood that the pass-through areas can be areas where the filament has been "threaded" through the papillary muscle (as depicted in FIG. 6C), or, alternatively, they can be openings in a device that is attached to the papillary muscle through which the filament can pass (such as a staple). First and second papillary pass-through areas are desirably on different papillary muscles. After passing through the first and second papillary pass-through areas, filament 35 is maneuvered to the second valve leaflet. The length of filament 35 can be adjusted by applying tension to the filament through catheter 26. Once the desired length is determined, the remaining end of filament 35 can be fixed to the second valve leaflet via second fastening mechanism 51. If desired, securing mechanisms, such as discussed above, can be placed at the locations of the first and second papillary pass-through areas 47, 53 to further secure filament 35.

It should be noted that the adjustment method discussed above and depicted in FIGS. 6C-6E could be modified as to the number of and location of the pass-through areas. For example, it may be desired to use two pass-through areas for the embodiment shown in FIG. 6C. Also, it may be desired to use only one pass-through area with the embodiment shown in FIG. 6F, such that two valve leaflets are connected to the same pass-through area.

Alternatively, it may be desirable to access the left atrium using an atriotomy procedure to replace, repair, or supplement the chordae tendinae as discussed above. Each of the methods discussed herein that generally depict accessing the left ventricle through the left atrium can also be achieved via an atriotomy. An atriotomy is a procedure where a surgical incision is made in the left atrium to access the heart. Accessing the mitral valve through an atriotomy can be desirable since such an approach provides an unencumbered view of the mitral annulus and subvalvular anatomy without damaging the surrounding structures. The particular location of the surgical incision in the wall of the left atrium can vary depending on a particular patient's anatomy and/or medical condition.

Figure 6G:
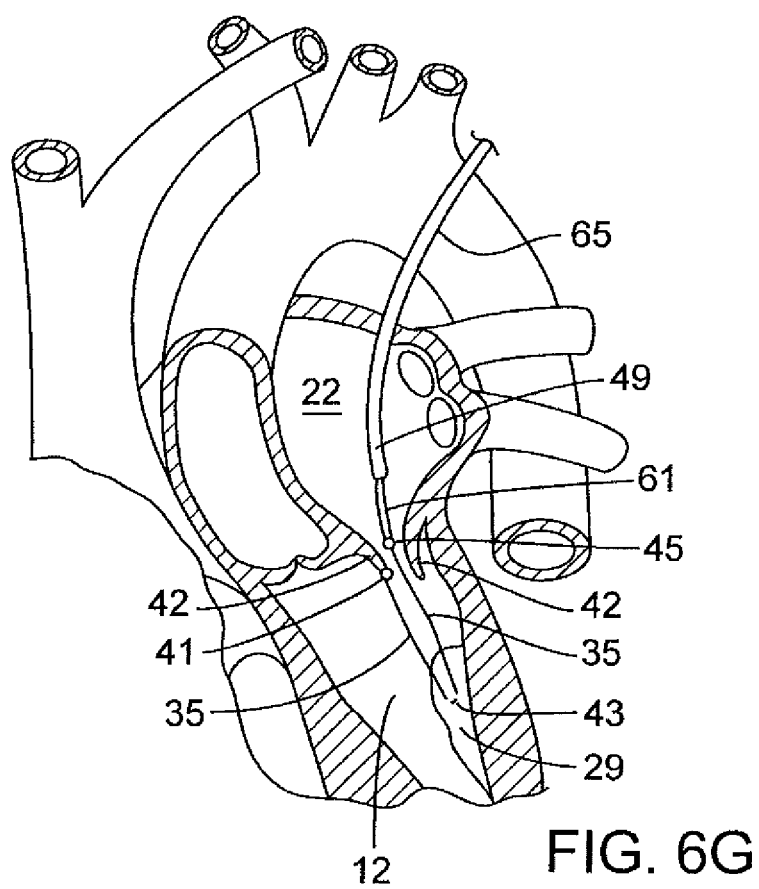
FIG. 6G is a sectional view of another embodiment of a method and apparatus for attaching artificial chordae to valve leaflets via an atriotomy.

FIG. 6G illustrates an embodiment similar to that shown in FIG. 6C-6E, except access to the heart is achieved through an atriotomy rather than via the patient's vasculature or the apex of the heart. As shown in FIG. 6G, a surgical incision can be made in the patient's chest and in the wall of the patient's left atrium 22. A tool 65 can be inserted into the chest, through the incision in the wall of the patient's left atrium 22, and into the left atrium 22 and left ventricle 12.

Tool 65 can be used to attach one end of a filament 35 to a valve leaflet 42 using first fastening mechanism 41. Tool 65 can then be maneuvered to an area near the papillary muscles 29 and filament 35 can be passed through a portion of the papillary muscles at a pass-through area 43. For convenience, a portion of the papillary muscles 29 are schematically represented in FIG. 6G. Tool 65 can then be withdrawn back into the left atrium. Because the filament will slide through the pass-through area of the papillary muscles, the length of filament 35 between fastening mechanism 41 and pass-through area 43 can be adjusted by pulling on the filament (i.e., adjusting the tension) using tool 65. In addition, because the physician has accessed the left atrium via an incision in the wall of the left atrium 22, the physician has a relatively unobstructed view of the mitral valve and can adjust the length of the filament while observing the heart in its natural state.

Once the physician is satisfied that with the desired length of filament 35, tool 65 (or another tool either separate or integral with tool 65) can be advanced down the filament and a securing mechanism 45 can be deployed to secure the filament to the papillary muscles. As noted above, U.S. Patent Publication No. 2004/0181238 (already incorporated by reference above) provides additional details for deploying such tools. As shown in FIG. 6F (with guide catheter 49 entering the left atrium via a transfemoral approach, however, rather than tool 65 entering the left atrium via an atriotomy), the securing mechanism 45 holds the filament securely at the papillary muscle 29, desirably at the location of the pass-through area, so that the length of the filament is substantially fixed. The securing mechanism can be any appropriate fastening, anchoring, or securing mechanisms, such as those disclosed herein. For example, the securing mechanism could be a clip holding the filament to the papillary muscle. After the securing mechanism is in place, the loose end of the filament 35 can be cut off and removed from the heart.

Although the temporary clipping or tying actions discussed above are particularly applicable during a transfemoral procedure or an atriotomy where it is desirable to withdraw a catheter from the left ventricle into the left atrium, they may also be useful in transapical procedures if the physician desires to retract a catheter from the heart in order to observe the heart in a more natural state.

FIGS. 7 and 8 show another embodiment utilizing artificial chordae to replace, repair, or supplement the native chordae tendinae to improve functioning of a heart valve. FIG. 7 depicts a triangular shaped member 70 that can be attached to a valve annulus at the short side 72 of the triangular shaped member and to a papillary muscle at the point 74 opposite the short side of the triangle. Alternatively, as shown in FIG. 8, the triangular shaped member can be a generally triangular shaped member 76 that is formed with two or more legs 78 opposite the short side 80 of the triangle. The triangular shaped member is desirably formed of a mesh or cloth or any other suitable biocompatible material.

FIG. 9 shows a valve 82 that includes a valve annulus 84 and valve leaflets 86, 88. The short side 72 of triangular shaped member 70 is attached to valve annulus 84. The point opposite the short side of triangular shaped member 70 extends between valve leaflets 86, 88 and attaches to a papillary muscle as shown in FIG. 10.

Figure 10:
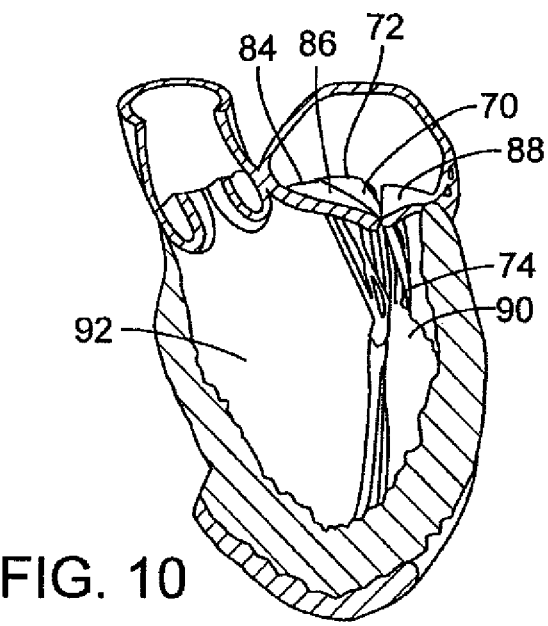
FIG. 10 is a sectional view of a triangular shaped member attached to a valve annulus and a papillary muscle.

FIG. 10 illustrates the attachment of triangular shaped member 70 to valve annulus 84 and papillary muscle 90. The short side 72 of triangular shaped member 70 can be sewn or otherwise attached to valve annulus 84. The point 74 opposite to the short side 72 of triangular member 70 can then be sewn or attached to a papillary muscle in the left ventricle 92, such as papillary muscle 90. The cloth or mesh triangular member 70 can tale the place of any number of native chordae that are elongated, broken, or otherwise damaged or not functioning properly.

Figure 11:
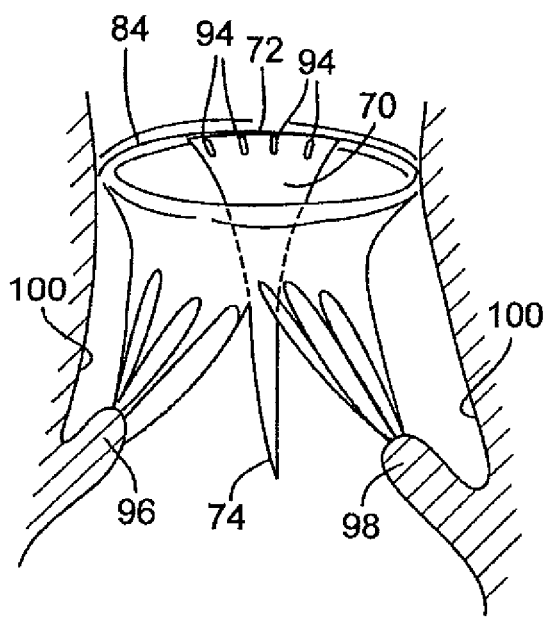
FIG. 11 is a perspective view of a triangular shaped member attached to a valve annulus.

FIG. 11 illustrates a method of attaching triangular shaped member 70 to valve annulus 84. Triangular shaped member 70 is shown in FIG. 11 attached to the valve annulus 84 but not yet attached to a papillary muscle. Short end 72 of triangular shaped member 70 is attached to valve annulus 84 by attachment mechanisms 94. Attachment mechanisms can be sutures or other known attachment means as discussed herein. The point 74 opposite to the short side 72 of triangular member 70 is shown unattached to any structure in FIG. 11, but it can be attached to the ventricle wall 100 or to a papillary muscle, such as papillary muscles 96, 98.

Figure 12:
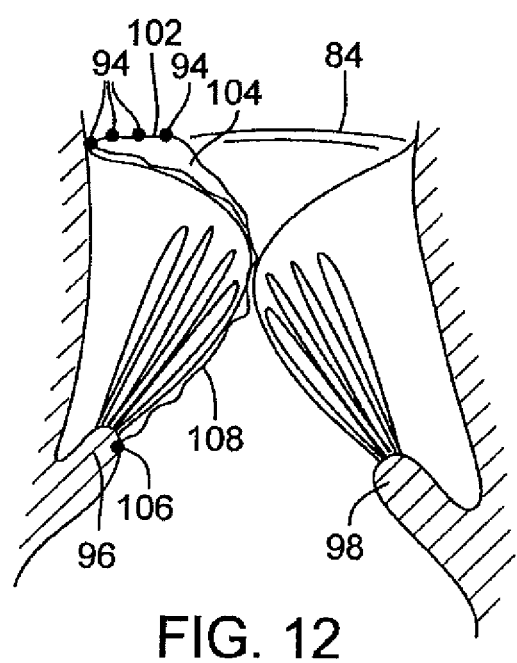
FIG. 12 is a perspective view of a triangular shaped member attached to a valve annulus and a papillary muscle.

FIG. 12 shows another embodiment of a triangular shaped member 104. The short side 102 of triangular shaped member 104 can be attached to valve annulus 84 via attachment mechanisms 94. The point opposite the short side 102 can be attached to a papillary muscle (such as papillary muscle 96) or ventricle wall using attachment mechanism 106. Attachment mechanism 94 can be any known attachment mechanism such as sutures, clips, or anchors, as discussed herein.

Triangular shaped member 104 further comprises a length adjustment member 108 that extends along at least a portion of the triangular shaped member 104 in a direction from the short side 102 to the lower end or point opposite the short side 102. Length adjustment member 108 can be a piece of length altering material such as a suture or string that can be pulled or otherwise adjusted to shorten or lengthen the triangular shaped member 104.

Length adjustment member 108 can have an upper end attached to the upper edge portion of member 104 and a lower end attached to or adjacent the lower end of member 104.

As shown in FIG. 12, for example, length adjustment member 108 can be a suture or string-like material that has excess slack so that upon the application of tension to length adjustment member 108 the effective length of the triangular shaped member can be shorted. Length adjustment member 108 permits adjustment to the effective length of the triangular shaped member 104 as measured from where the short side 102 is attached to the valve annulus to the other point of attachment at attachment mechanism 106. Alternatively, the effective length of the triangular shaped member can be adjusted by sewing up slack (or otherwise removing slack by altering the attachment locations of the triangular shaped member) at the annulus or papillary muscle.

Alternatively, the triangular shaped member can have a ring or a portion of a ring sewn on or attached to the short side of the triangular shaped member. The ring portion can aid in reshaping the annulus.

The implantation of the triangular shaped member can be performed in a variety of ways. For example, the triangular shaped member can be implanted using a transapical method, a transfemoral method, or via an open surgery.

Figure 13A:
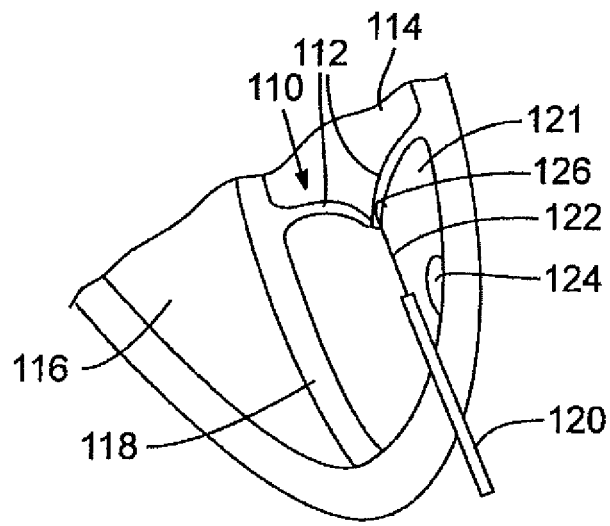
FIG. 13A is a view of an embodiment of a method and apparatus for attaching artificial chordae to a valve leaflet.
Figure 13B:
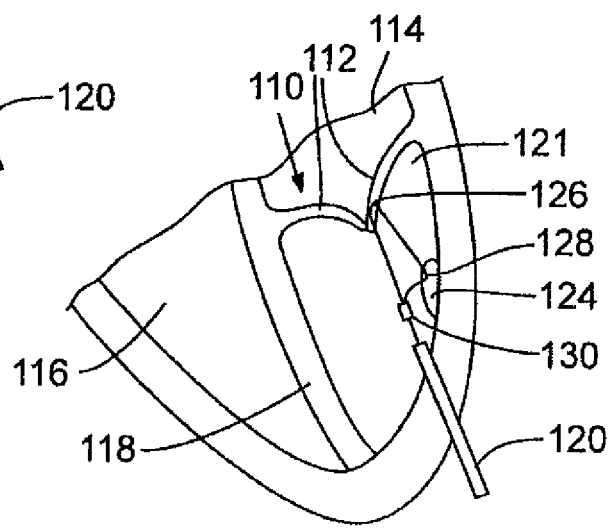
FIG. 13B is a view of an embodiment of a method and apparatus for attaching artificial chordae to a valve leaflet.
Figure 13C:
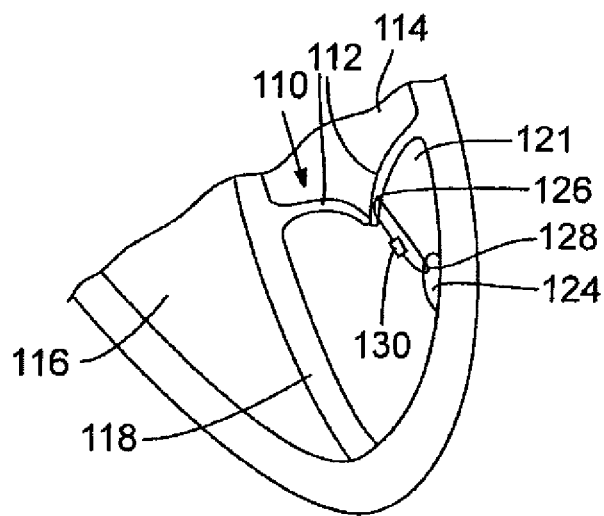
FIG. 13C is a view of an embodiment of a method and apparatus for attaching artificial chordae to a valve leaflet.

FIGS. 13A-13C illustrate another method for performing minimally invasive mitral valve repair using a transapical procedure. FIG. 13A illustrates mitral valve 110, valve leaflets 112, left atrium 114, right ventricle 116, and septum 118. A catheter 120 is deployed transapically (desirably via an introducer sheath, not shown for clarity) into left ventricle 121. As shown in FIG. 13A, a first end of a suture 122 (filament) is stitched or otherwise attached to a valve leaflet 112 at attachment location 126.

Referring to FIG. 13B, after attaching suture 122 to valve leaflet 112, the catheter 120 is positioned at or near a papillary muscle 124 and the first end of suture 122 is then stitched or otherwise attached to the papillary muscle 124. Desirably, suture 122 is attached to the papillary muscle using a "movable" stitch 128, also known as a "soft anchor."

Desirably, the first end of suture 122 passes back through catheter 120 so that the length of the suture between the papillary muscle and the leaflet can be adjusted manually.

The first end of suture 122 then passes through securing device 130. Securing device 130 can be any means of securing the suture 122 to itself, such as a zip-tie or other type of attaching or clamping mechanism. Alternatively, suture 122 can be secured to itself using a slipknot or other tying mechanism.

The length of suture 122 between the papillary muscle and the leaflets is observed to determine whether the proper length has been chosen. If not, the length can be adjusted accordingly. Once it is determined that the appropriate length has been achieved, the securing mechanism 130 is secured so that the length of suture 122 is fixed. Excess suture material can then be removed and, if the procedure is complete and no other sutures are to be implanted, the catheter 120 can be withdrawn from the left ventricle 121, as shown in FIG. 13C.

Figures 14A, 14B:
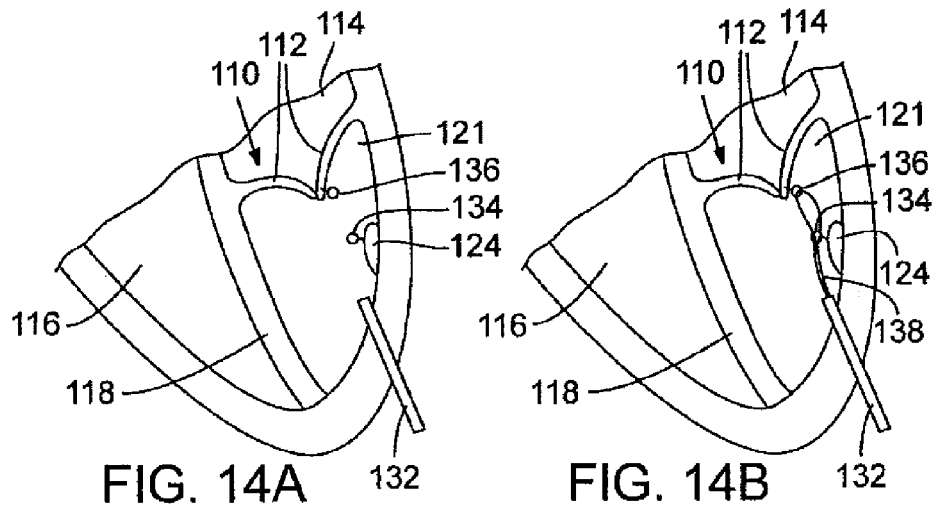
FIG. 14A is a view of an embodiment of a method and apparatus for attaching artificial chordae to a valve leaflet.
FIG. 14B is a view of an embodiment of a method and apparatus for attaching artificial chordae to a valve leaflet.

FIGS. 14A-14D illustrate another method for performing minimally invasive mitral valve repair using a transapical procedure. FIG. 14A illustrates mitral valve 110, valve leaflets 112, left atrium 114, right ventricle 116, septum 118, and right ventricle 121. A catheter 132 is deployed transapically (desirably via an introducer sheath, not shown) into left ventricle 121. Catheter 132 is deployed to a papillary muscle 124 and a first anchor device 134 is secured to papillary muscle 124. Catheter 132 is then maneuvered to a valve leaflet 112. The valve leaflet 112 is captured and a second anchor device 136 is secured to valve leaflet 112. The first and second anchor devices have an eyelet or other opening to receive a suture.

Referring to FIG. 14B, catheter 132 is retracted or withdrawn back to papillary muscle 124 to a position near the first anchor device 134. A suture 138 is delivered via catheter 132 and a first end of the suture is passed through the eyelet of first anchor device 134. Catheter 132 is then maneuvered to a position near second anchor device 136 and the first end of suture 138 is passed through the eyelet of second anchor device 136. Catheter 132 is once again maneuvered back to a position near second anchor device 136 and the first end of suture 138 is again passed through the eyelet of first anchor device 134, forming a suture loop (filament loop) between the two anchor devices.

The length of the suture between the eyelets of the first and second anchor devices 134, 136 can be adjusted by adjusting tension of the suture through the catheter. Desirably, the first end of the suture is passed back through the catheter to facilitate manual adjustment of the tension in the suture loop. Once the proper length of suture 138 is achieved a clip 140 (or other securing mechanism) can be placed at first anchor device 134 securing suture 138 in place. The clip 140 is desirably passed through catheter 132 and down suture 138 to first anchor device 134. Excess suture material can then be removed and, if the procedure is complete and no other sutures are to be implanted, catheter 132 can be withdrawn from left ventricle 121.

Figures 14C, 14D:
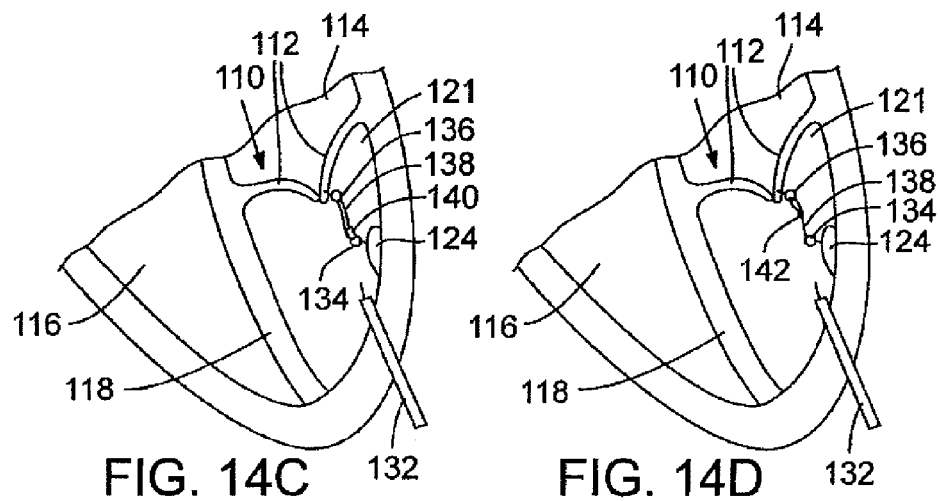
FIG. 14C is a view of an embodiment of a method and apparatus for attaching artificial chordae to a valve leaflet.
FIG. 14D is a view of an embodiment of a method and apparatus for attaching artificial chordae to a valve leaflet.

Alternatively, as shown in FIG. 14D, the suture can be secured to itself using weld 142. In this approach, it may be desirable to tie or otherwise attach suture 138 to first anchor device 134 and then pass it through the eyelet of second anchor device 136. Suture 138 can then be passed back through catheter 132 and the length of the suture can be adjusted as described above. Once the appropriate length is determined, suture 138 can be secured by welding it to itself at weld 142.

Alternatively, suture 138 need not be secured to the first anchor device as described above. Rather, a suture loop can be formed and the suture can be secured to itself without attaching the suture to the anchor devices (other than passing through the eyelets of the anchor devices).

It should be noted that the order of attaching the anchor devices can vary. For example, an anchor device can be secured to a leaflet first and then a second anchor device can be secured to a papillary muscle, and vice versa. In addition, if a suture loop is to be formed, the suture loop can be formed by looping the suture first through the first anchor device and then through the second anchor device, or vice versa.

The methods discussed above depict both transapical and transfemoral approaches for placement of artificial chordae. It should be understood, however, that the techniques described above can be generally applied to methods other than those discussed above, so long as the approach results in access to the left ventricle. For example, the techniques discussed above are applicable if the left ventricle is accessed via the femoral artery and the aorta.

Also, for each embodiment described above where a device is shown or described as being attached to a papillary muscle, it should be understood that the attachment can alternatively be to another papillary muscle (other than the papillary muscle shown) or to the ventricle wall itself.

Desirably, in each of the above-described procedures a physician can observe the beating heart of the patient during the procedure to determine whether the length or position of the artificial chords (e.g., filaments or sutures) should be adjusted. Such observation of the heart can be achieved by any known imaging technology.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of performing mitral valve chordal repair on a patient while the patient's heart is beating, the method comprising:
    making an incision in a ventricular wall of the patient;
    inserting a catheter through the incision into a left ventricle of the patient;
    navigating a distal end of the catheter to a mitral valve leaflet of the patient, the catheter containing at least one filament, the filament having a first end and a second end;
    passing the first end of the filament through an eyelet of a first attachment point at the mitral valve leaflet, the eyelet being sized to allow the filament to move relative to the eyelet;
    navigating the distal end of the catheter to a position at or near a papillary muscle, the position being at or near a second attachment point on the papillary muscle;
    passing the first end of the filament through the second attachment point;
    adjusting the length of the filament by adjusting tension of the filament in the catheter;
    passing the first end of the filament through a securing device;
    securing the first end of the filament to another portion of the filament within the left ventricle using the securing device to form a filament loop entirely within the left ventricle;
    removing excess material from the filament loop; and
    withdrawing the catheter from the left ventricle.

2. The method of claim 1, wherein the step of adjusting the length of the filament further comprises passing the first end of the filament into the catheter to facilitate manual adjustment of tension of the filament in the catheter.

3. The method of claim 1, wherein the second attachment point comprises a moveable stitch.

4. The method of claim 1, wherein the securing device comprises a zip-tie device.

5. The method of claim 1, wherein adjusting the length of the filament by adjusting tension of the filament in the catheter comprises changing the length of the filament between the first and second attachment points, the filament being movable relative to both of the first and second attachment points.

6. The method of claim 1, wherein the incision is made at or near the apex of the heart.

7. The method of claim 1, wherein the act of securing the first end of the filament to another portion of the filament within the left ventricle using the securing device comprises delivering the securing device through the catheter and securing the securing device to the first end of the filament and the another portion of the filament.

8. A method of performing mitral valve chordal repair on a patient while the patient's heart is beating, the method comprising:
    making an incision in a ventricular wall of the patient;
    inserting an introducer sheath through the incision to provide access to a left ventricle of the patient;
    delivering a catheter through the introducer sheath to a vicinity of a papillary muscle of the patient and attaching a first anchor device to the papillary muscle of the patient, the first anchor device comprising an eyelet for receiving a filament;
    moving the catheter to a vicinity of a mitral valve leaflet of the patient and attaching a second anchor device to the mitral valve leaflet of the patient, the second anchor device comprising an eyelet for receiving the filament;
    forming a filament loop between the first and second anchor devices by passing a first end of the filament out of the catheter and through the eyelet of the first anchor device and the eyelet of the second anchor device;
    passing the first end of the filament back into the catheter after forming the filament loop;
    adjusting the length of the filament between the first and second anchor devices by adjusting the tension of the filament in the catheter;
    passing the first end of the filament through a securing device;
    fixing the length of the filament between the first and second anchor devices by attaching the securing device to the filament within the left ventricle to form the filament loop entirely within the left ventricle; and
    withdrawing the catheter from the left ventricle.

9. The method of claim 8, wherein the securing device comprises a clip secured to the filament at the first anchor device.

10. The method of claim 8, wherein the securing device comprises a weld, the weld securing the filament to itself at a point along the filament loop.

11. The method of claim 8, wherein passing the first end of the filament through the eyelet of the second anchor device results in a portion of the filament extending between the eyelets of the first and second anchor devices.

12. The method of claim 8, wherein the adjusting the length of the filament comprises adjusting the length of the filament between the eyelets of the first and second anchor devices, and wherein the filament is movable relative to each eyelet.

13. A method of performing mitral valve chordal repair on a patient while the patient's heart is beating, the method comprising:
    making an incision in a ventricular wall of the patient;
    inserting an introducer sheath system through the incision to provide access to a left ventricle of the patient;
    attaching a first anchor device to a mitral valve leaflet of the patient, the first anchor device comprising an eyelet for receiving a filament;
    attaching a second anchor device to a papillary muscle of the patient, the second anchor device comprising an eyelet for receiving a filament;

inserting a distal end of a catheter through the introducer sheath system, the catheter containing at least one filament, the filament having a first end and a second end;

navigating the distal end of the catheter to the first anchor device;

passing the first end of the filament through the eyelet of the first anchor device;

navigating the distal end of the catheter to the second anchor device;

passing the first end of the filament through the eyelet of the second anchor device so that a portion of the filament extends between the eyelets of the first and second anchor device;

adjusting the length of the filament by adjusting tension of the filament in the catheter while the catheter is within the left ventricle, the filament being movable relative to both the first and second anchor devices; and securing the first end of the filament to an intermediate portion of the filament to form a filament loop entirely within the left ventricle; and withdrawing the catheter from the left ventricle.

14. The method of claim 13, wherein the incision is made at or near the apex of the heart.

* * * * *